United States Patent [19]
Burrows et al.

[11] Patent Number: 6,048,365
[45] Date of Patent: Apr. 11, 2000

[54] IMPLANTABLE ORTHOPEDIC PROSTHESIS HAVING KEYED TAPER CONNECTOR

[75] Inventors: James W. Burrows, Austin; Erin M. Johnson, Round Rock, both of Tex.

[73] Assignee: Sulzer Orthopedics Inc., Austin, Tex.

[21] Appl. No.: 09/053,584

[22] Filed: Apr. 1, 1998

[51] Int. Cl.[7] ................................................ A61F 2/36
[52] U.S. Cl. ............................................................ 623/23
[58] Field of Search ................................ 623/22, 23, 19

[56] References Cited

U.S. PATENT DOCUMENTS

| | | | |
|---|---|---|---|
| 4,946,379 | 8/1990 | Berchem | 623/18 |
| 4,957,510 | 9/1990 | Cremascoli | 623/23 |
| 4,963,155 | 10/1990 | Lazzeri et al. | 623/23 |
| 5,100,407 | 3/1992 | Conrad et al. | 606/79 |
| 5,156,624 | 10/1992 | Barnes | 623/22 |
| 5,405,403 | 4/1995 | Mikhail | 623/22 |
| 5,480,451 | 1/1996 | Grundei et al. | 623/23 |
| 5,597,384 | 1/1997 | Walker et al. | 623/66 |

*Primary Examiner*—David H. Willse
*Attorney, Agent, or Firm*—Philip S. Lyren; Kenneth S. Barrow

[57] ABSTRACT

A set of modular components from among which an implantable orthopedic hip prosthesis can be assembled. First and second implantable orthopedic femoral hip stem prosthesis each have a neck, the neck having a male conical taper surface. An implantable orthopedic femoral head prosthesis has a female conical taper surface. The respective male and female conical taper surfaces are sized and configured for mutual taper-locked interconnection if engaged, but at least one of the first and second implantable orthopedic femoral hip stem prosthesis is keyed in combination with the implantable orthopedic femoral head prosthesis to prevent engagement of the respective male conical taper surface with the female conical taper surface.

21 Claims, 4 Drawing Sheets

IMPLANTABLE ORTHOPEDIC PROSTHESIS HAVING KEYED TAPER CONNECTOR

BACKGROUND OF THE INVENTION

1. Field of the Invention

This invention relates generally to implantable prostheses for replacing human skeletal joints, and relates more particularly to implantable prostheses having friction-locking taper connections between components.

2. Background Information

Occasionally, one of the articulating skeletal joints of the human body fails to function normally as a result of disease, trauma, or congenital defect. Often, the failure is related to abnormalities in the articulating surfaces at the ends of the bones comprising the joint. In many such cases, the joint can be repaired or reconstructed by replacing the involved ends and articulating surfaces with manufactured implantable prostheses. The hip joint is among the joints most often treated with such prostheses.

The human hip joint involves two bones: the femur and the pelvis, each having a smooth articulation surface arranged for articulation against an adjacent articulation surface of the other bone. The femur includes at its proximal extremity a head having a convex, generally spherically contoured articulation surface. The pelvis, in pertinent part, includes an acetabulum having a concave, generally spherically contoured articulation surface. The mutually engaging articulation surfaces of the femur and the pelvis together form, functionally, a ball-and-socket joint.

One or both of the articulation surfaces of the hip joint may fail to perform normally, requiring the defective natural articulation surface to be replaced with a prosthetic articulation surface provided by an implantable orthopedic prosthesis. To fit defects of varying scope, while allowing healthy portions of the hip joint to be conserved, a range of types of orthopedic implants is available. The range extends from total hip prosthesis systems for replacing the articulation surfaces of both the femur and the pelvis, to simpler systems for replacing only the femoral articulation surface.

Commonly employed orthopedic hip prostheses include components that fall within one of three principle categories: femoral stems, femoral heads and acetabular cups. A so-called "total" hip prosthesis includes components from each of these categories. The femoral stem replaces the proximal end of the femur and includes a distal stem received within the medullary canal at the proximal end of the femur. The femoral head replaces the natural head and articulating surface of the femur. The acetabular cup replaces the natural socket and articulating surface of the acetabulum of the pelvis. In some designs, the stem and head are an integral, unitary component, but more often the stem and head are separate modular components designed to be assembled to suit the anatomical needs of the patient. Typically, the stem includes an integral neck portion that is assembled to the head component through a friction-locked taper connection, also known as a Morse taper. Several stems and heads, of differing sizes or configurations but having a commonly configured taper connector, can be provided to allow many different combinations of stem and head. Usually, the neck of the stem is provided with a male conical taper-locking surface and the head is provided with a complementary female conical taper-locking surface.

Head components can be varied both with regard to diameter, and with regard to the location of the center of the head relative to the stem component. The former variation is self-explanatory, whereas the latter variation is accomplished by varying the depth of placement of the female conical taper within the head. The shallower the depth of placement of the female conical taper, the greater the displacement of the center of the head from the stem when the head and stem components are assembled. A shallower placement of the female conical taper of the head results in an effective lengthening of the neck portion of the stem. For a given stem, a chosen depth of female taper in the head is designated as having a plus zero (+0) effect on neck length. Heads having shallower depths of female tapers, when mated with the particular stem, can provide extensions of the basic neck length, and are designated by the amount of neck extension they provide, e.g., plus ten millimeters (+10 mm). To assure sufficient mating surface between the male and female taper-locking surfaces, the head can be provided with an integral collar that extends from the head and surrounds the female conical taper.

Extending the effective length of the neck of a hip stem, by using a head having a shallowly placed female conical taper, increases the distance at which loads are applied to the stem through the head. This increased distance, or lever arm, with some combinations of stems and heads, can result in moment forces that exceed the design parameters of the stem. It would be desirable to provide a way to prevent assembly in the field of undesirable combinations of stems and heads. The present invention achieves this and other desirable goals.

SUMMARY OF THE INVENTION

According to one aspect of the present invention, a set of modular components are provided from among which an implantable orthopedic hip prosthesis can be assembled. The set includes a first implantable orthopedic femoral hip stem prosthesis having a neck with a male conical taper surface, and a second implantable orthopedic femoral hip stem prosthesis having a neck with a male conical taper surface. Also included is an implantable orthopedic femoral head prosthesis having a female conical taper surface. The respective male and female conical taper surfaces are sized and configured for mutual taper-locked interconnection if engaged. At least one of the first and second implantable orthopedic femoral hip stem prosthesis is keyed in combination with the implantable orthopedic femoral head prosthesis to prevent engagement of the respective male conical taper surface with the female conical taper surface.

An object of the invention is to prevent field assembly of inadvisable combinations of modular head and stem components from a set of components.

Other objects and advantages of the invention will be apparent from the following descriptions of preferred embodiments of the invention, made with reference to the drawings.

DETAILED DESCRIPTION OF THE PREFERRED EMBODIMENT

Figure 1:
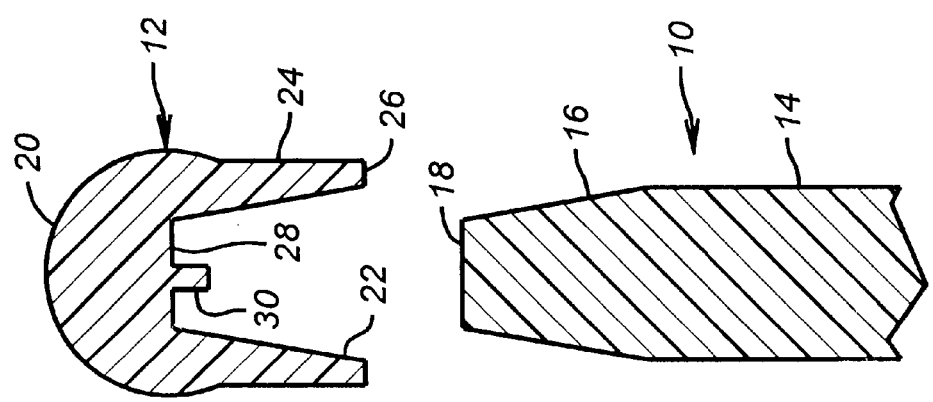
FIG. 1 is a longitudinal-section view of the neck portion of an implantable orthopedic femoral stem prosthesis and a modular femoral head prosthesis.

Referring to FIG. 1, a portion of a hip stem 10 and a head 12 are shown. Hip stem 10 includes, in pertinent part, a neck 14 having a male conical taper surface 16 terminating in a planar end face 18. The configuration of hip stem 10 as illustrated in FIG. 1 is typical of commonly available modular hip stems. Head 12 includes a generally convex spherical articulating surface 20 and a female conical taper surface 22. A cylindrical collar 24 extends radially from head 12 and terminates in an end face 26. Collar 24 surrounds female conical taper surface 22, which forms an opening at annular end face 26. Conical taper surface 22 terminates at a closed interior end 28. As described so far, head 12 is typical of commonly available modular femoral heads. Differing from typical heads, head 12 includes a cylindrical pin 30 extending from closed interior end 28 coaxial with female conical taper surface 22. Pin 30 is of such length as to prevent head 12 from fulling seating in taper-locked engagement with stem 10. Pin 30 engages end face 18 of stem 10 before female taper surface 22 has engaged male taper surface 16 in congruent mating relationship, thereby preventing head 12 from being effectively coupled to stem 10.

Figure 2:
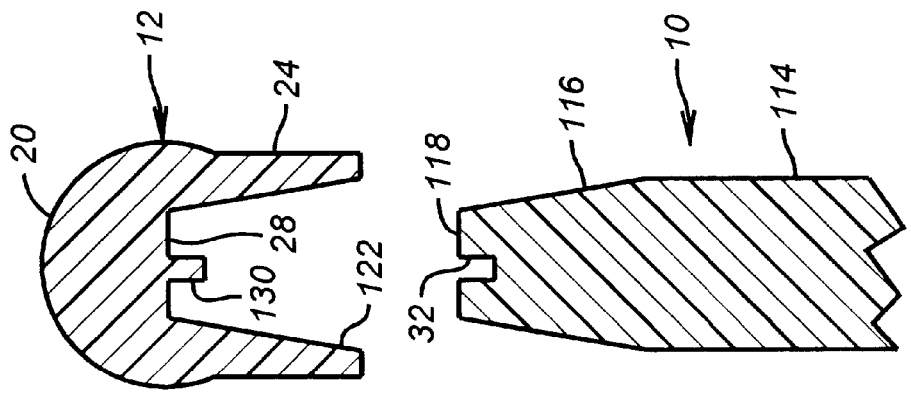
FIG. 2 is a longitudinal-section view of the neck portion of an alternative implantable orthopedic femoral stem prosthesis and the modular femoral head prosthesis of FIG. 1.

Referring to FIG. 2, an second putative stem and head combination is shown, with those portions that are substantially similar to corresponding portions of the embodiment of FIG. 1 being designated by like reference numerals in the 100 series. For example, stem 110 of FIG. 2 is substantially similar to stem 10 of FIG. 1 except for a cylindrical recess 32 disposed in end face 118 coaxial with male conical taper surface 116. Recess 32 is of sufficient diameter and depth to receive pin 130 therein without interference, such that female conical surface 122 can fully engage male conical surface 116 in congruent friction-locked relationship. The depth of recess 32 must be sufficiently great that pin 130 cannot bottom out before male and female conical surfaces 116 and 122 are fully engaged.

Considered together, the embodiments of FIGS. 1 and 2 can be regarded as a modular system comprising a head 12 and a pair of stems 10 and 110. As configured, head 12 can be fitted to stem 110, but not to stem 10. This characteristic can be exploited in designing a set of modular components to prevent particular heads from being combined with particular stems. For example, one may wish to include in a set an optional head providing a +12 mm extension, and yet wish to prevent inadvisable combinations of that head with certain stems. This can be accomplished by providing the +12 mm head with a pin 30 or 130, and providing only compatible stems with a corresponding recess 32. All other heads and stems in the set would be conventionally configured, such as stem 10 of FIG. 1 and head 12 less pin 30.

Figure 5:
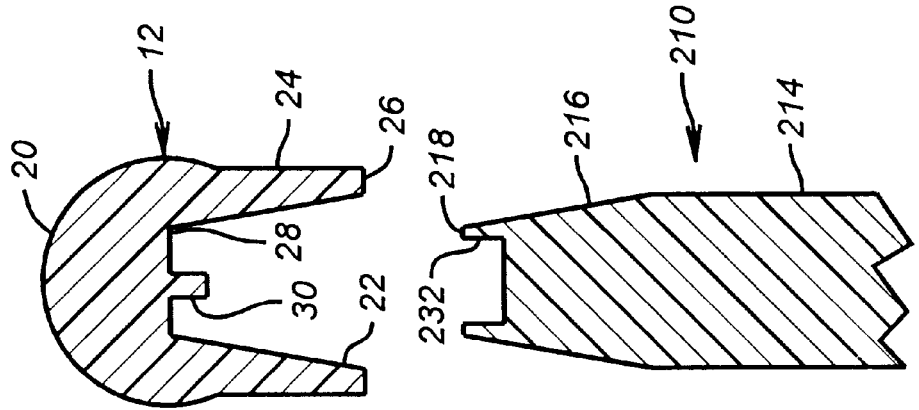
FIG. 5 is a longitudinal-section view of the neck portion of the second alternative implantable orthopedic femoral stem prosthesis of FIG. 4 and modular femoral head prosthesis of FIG. 1.
Figure 4:
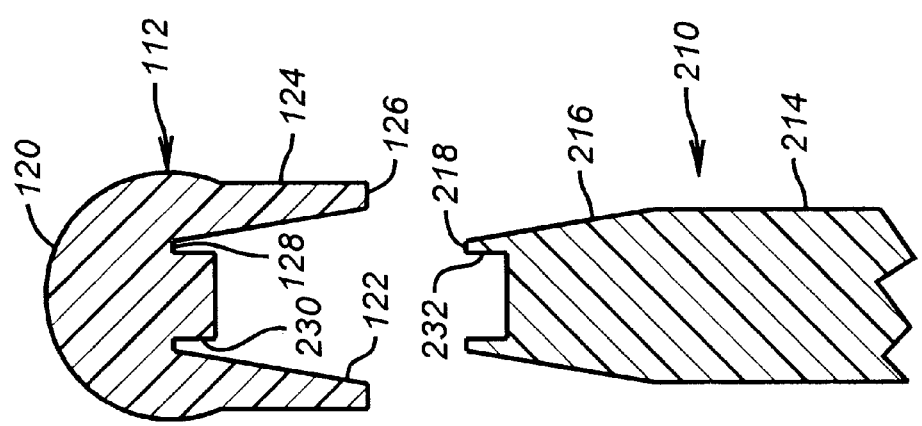
FIG. 4 is a longitudinal-section view of the neck portion of a second alternative implantable orthopedic femoral stem prosthesis and the alternative modular femoral head prosthesis of FIG. 3.
Figure 3:
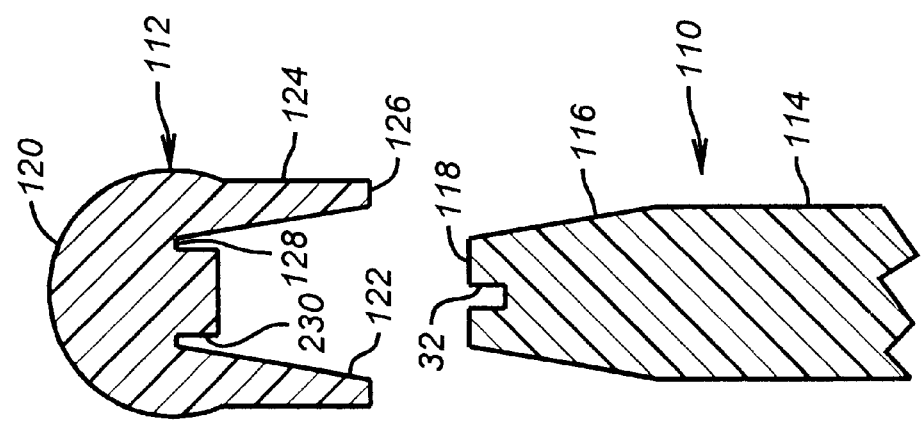
FIG. 3 is a longitudinal-section view of the neck portion of the implantable orthopedic femoral stem prosthesis of FIG. 2 and an alternative modular femoral head prosthesis.
Figure 9:
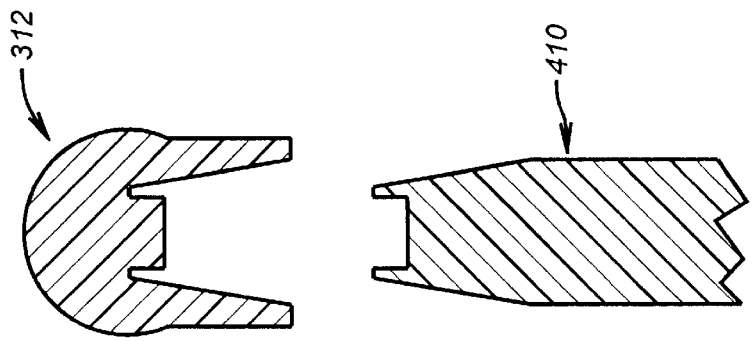
FIG. 9 is a longitudinal-section view of the neck portion of the fourth alternative implantable orthopedic femoral stem prosthesis and the fourth alternative modular femoral head prosthesis of FIG. 7.
Figure 8:
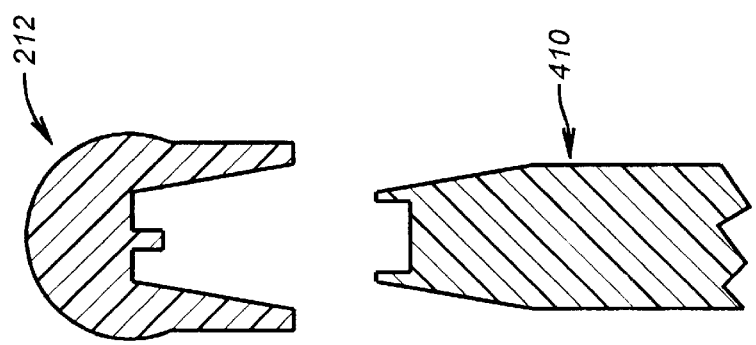
FIG. 8 is a longitudinal-section view of the neck portion of a fourth alternative implantable orthopedic femoral stem prosthesis and the third alternative modular femoral head prosthesis of FIG. 6.
Figure 7:
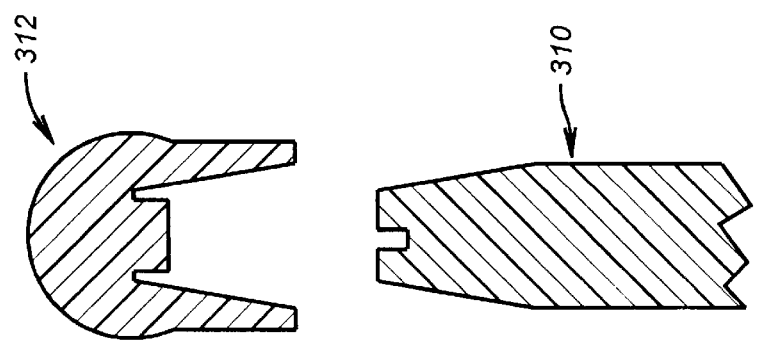
FIG. 7 is a longitudinal-section view of the neck portion of the third alternative implantable orthopedic femoral stem prosthesis of FIG. 6 and a fourth alternative modular femoral head prosthesis.
Figure 6:
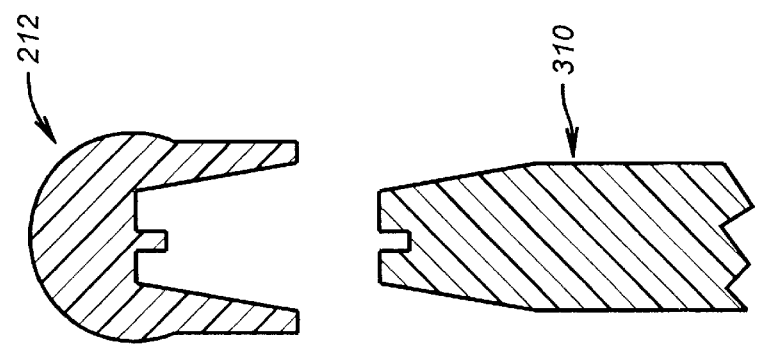
FIG. 6 is a longitudinal-section view of the neck portion of a third alternative implantable orthopedic femoral stem prosthesis and a third alternative modular femoral head prosthesis.

Referring to FIGS. 3, 4 and 5, further variations of the invention are shown that permit more complex limitations on the permissible combinations of stem and head. Portions of components that are similar to previously described components are designated by like reference numerals in the 100 and 200 series. In FIG. 3, a putative combination is shown comprising stem 110 of FIG. 2 and a head 112 that is substantially similar to head 12, with the exception that pin 230 has a diameter significantly greater than that of pin 30 and that of recess 32. Consequently, head 112 cannot be fitted to either stem 10 or stem 110. In FIG. 4, a putative combination is shown comprising head 112 of FIG. 3 and a stem 210 that is substantially similar to stem 110, except that recess 232 is of sufficient depth and diameter to receive pin 230 without interference, permitting full engagement of the male and female taper locking surfaces 216 and 122. In FIG. 5, a putative combination is shown comprising head 12 of FIG. 1 and stem 210 of FIG. 4. Coincidentally, recess 232 can receive pin 30 of head 12 without interference, permitting full engagement of the male and female taper locking surfaces 216 and 22.

Considered together, the embodiments of FIGS. 1, 2, 3, 4 and 5 can be regarded as a modular system comprising a pair of heads 12 and 112, and three alternative stems 10, 110 and 210. As configured, head 12 can be fitted to stems 110 and 210, but not to stem 10. Likewise, head 112 can be fitted to stem 210, but not to stems 10 and 110.

Referring to FIGS. 6, 7, 8 and 9, alternative embodiments of the above-described components are shown in which the gender of the keying components has been reversed. Features that are similar to previously described embodiments are designated by like reference numerals in the 200, 300 and 400 series, with the understanding that components described as pins with respect to FIGS. 1–5 comprised recesses in FIGS. 6–9, and components described as recesses with respect to FIGS. 1–5 comprise recesses in FIGS. 6–9. In short, stem 310 (and stem 10 of FIG. 1) can receive heads 212 and 312, and stem 410 can receive only head 312.

Figure 12:
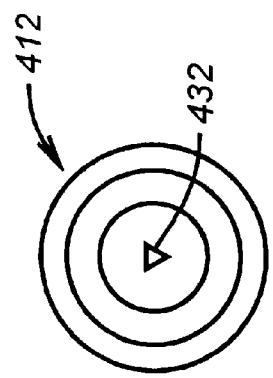
FIG. 12 is a cross-sectional view of the fifth alternative moduluar femoral head prosthesis of FIG. 10.
Figure 10:
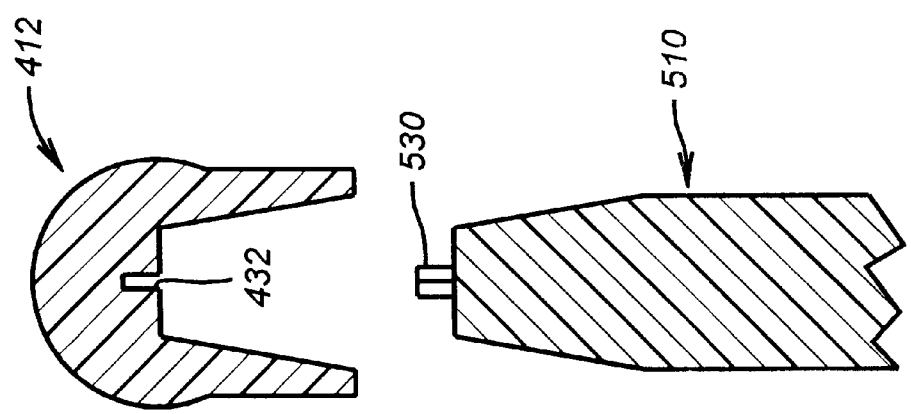
FIG. 10 is a longitudinal-section view of the neck portion of a fifth alternative implantable orthopedic femoral stem prosthesis and a fifth alternative modular femoral head prosthesis.

Referring to FIGS. 10 and 12, alternative embodiments of the above-described components are illustrated as stem 510 and modular head 412, in which the mating pin 530 and recess 432 are triangular in cross-section, rather than cylindrical. In addition to the advantages described above for the previous embodiments, this configuration provides constraint against rotation of modular head 412 relative to stem 510. Alternatively, pin 530 and recess 432 could have any non-round polygonal cross-section.

Figure 11:
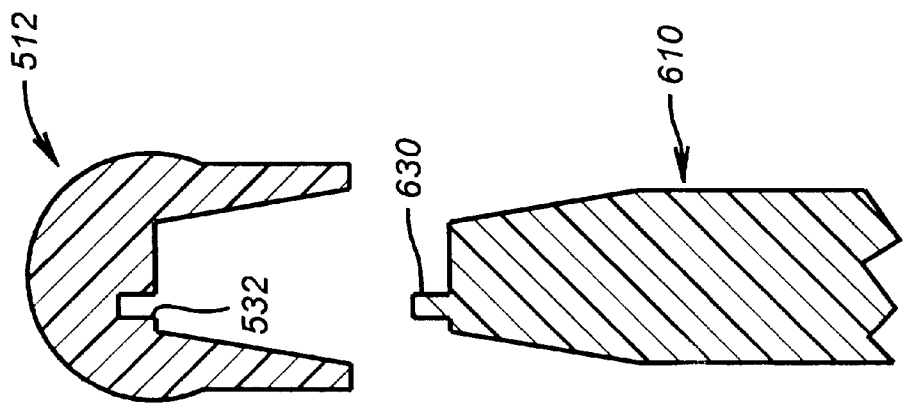
FIG. 11 is a longitudinal-section view of the neck portion of a sixth alternative implantable orthopedic femoral stem prosthesis and a sixth alternative modular femoral head prosthesis.

Referring to FIG. 11, alternative embodiments of the above-described components are illustrated as stem 610 and modular head 512, in which the mating pin 630 and recess 532 are located eccentrically relative to the longitudinal axis of symmetry of stem 610 and modular head 512. Like the embodiment of FIGS. 10 and 12, this configuration also provides constraint against rotation of modular head 412 relative to stem 510. Pin 630 and recess 532 can have a round cross-section or can have any non-round polygonal cross-section.

It should be appreciated that the range of permissible and impermissible combinations can be extended by providing further sizes of pin and recess diameters, and also by providing pins and recesses of various lengths and depths.

The present invention has been illustrated and described with particularity in terms of a preferred embodiment. Nevertheless, it should be understood that no limitation of the scope of the invention is intended. The scope of the invention is defined by the claims appended hereto. It should also be understood that variations of the particular embodiments described herein incorporating the principles of the present invention will occur to those of ordinary skill in the art and yet be within the scope of the appended claims.

I claim:

1. A set of modular components from among which an implantable two-piece orthopedic hip prosthesis can be assembled, comprising:
    a first implantable orthopedic femoral hip stem prosthesis having a neck, said neck having a male conical taper surface;
    a second implantable orthopedic femoral hip stem prosthesis having a neck, said neck having a male conical taper surface; and
    an implantable orthopedic femoral head prosthesis connectable directly onto at least one of the first and second implantable orthopedic femoral hip stem prostheses and having an opening with a key located inside said opening, said opening having a female conical taper surface;
    said respective male and female conical taper surfaces being sized and configured for mutual taper-locked interconnection if engaged to form said two-piece orthopedic hip prosthesis;
    at least one of said first and second implantable orthopedic femoral hip stem prostheses being keyed in combination with said key in said opening to prevent engagement of the respective male conical taper surface with the female conical taper surface.

2. The set of modular components of claim 1, in which said keyed stem and head prostheses include a pin extending from said head inwardly of said female conical taper surface.

3. The set of modular components of claim 2, in which said pin extends axially from said head coaxial with said female conical taper surface.

4. A set of modular components from among which an implantable two-piece orthopedic hip prosthesis can be assembled, comprising:
    a first implantable orthopedic femoral hip stem prosthesis having a neck, said neck having a male conical taper surface;
    a second implantable orthopedic femoral hip stem prosthesis having a neck, said neck having a male conical taper surface;
    a first implantable orthopedic femoral head prosthesis and a second implantable orthopedic femoral head prosthesis, each femoral head prosthesis connectable directly onto at least one of the first and second implantable orthopedic femoral hip stem prostheses and having an opening with a key located inside said opening, said opening having a female conical taper surface;
    said respective male and female conical taper surfaces being sized and configured for mutual taper-locked interconnection if engaged to form said two-piece orthopedic hip prosthesis;
    at least one of said first and second implantable orthopedic femoral hip stem prostheses being keyed in combination with said key in said opening of said first and second implantable orthopedic femoral head prosthesis to prevent engagement of the respective male conical taper surface with at least one but not all of the female conical taper surfaces.

5. The set of modular components of claim 4, in which said keyed stem and head prostheses include a pin extending from at least one said head inwardly of said female conical taper surface.

6. The set of modular components of claim 5, in which said pin extends axially from said head coaxial with said female conical taper surface.

7. The set of modular components of claim 4, in which each of said head prostheses includes a pin extending from said head inwardly of said female conical taper surface.

8. The set of modular components of claim 7, in which each of said stem prostheses includes a recess in said neck inwardly of said male conical taper surface.

9. The set of modular components of claim 8, in which said pins of at least two of said modular head prostheses are differently sized.

10. The set of modular components of claim 9, in which the recess of at least one of said modular stem prostheses is sized to receive the pin of at least one but not all of the said modular head prostheses.

11. A set of modular components from among which an implantable two-piece orthopedic hip prosthesis can be assembled, comprising:
    a first implantable orthopedic femoral hip stem prosthesis having a neck, said neck having a male conical taper surface;
    a second implantable orthopedic femoral hip stem prosthesis having a neck, said neck having a male conical taper surface;
    a first implantable orthopedic femoral head prosthesis and a second implantable orthopedic femoral head prosthesis, each femoral head prosthesis connectable directly onto at least one of the first and second implantable orthopedic femoral hip stem prostheses and having an opening with a key located inside said opening, said opening having a female conical taper surface;
    said respective male and female conical taper surfaces being sized and configured for mutual taper-locked interconnection if engaged to form said two-piece orthopedic hip prosthesis;
    at least one of said keys in said opening of said first and second implantable orthopedic femoral head prosthesis being keyed in combination with said first and second implantable orthopedic femoral stem prosthesis to prevent engagement of the respective female conical taper surface with at least one but not all of the male conical taper surfaces.

12. The set of modular components of claim 11, in which said keyed stem and head prostheses include a pin extending from at least one said head inwardly of said female conical taper surface.

13. The set of modular components of claim 12, in which said pin extends axially from said head coaxial with said female conical taper surface.

14. The set of modular components of claim 13, in which each of said head prostheses includes a pin extending from said head inwardly of said female conical taper surface.

15. The set of modular components of claim 14, in which each of said stem prostheses includes a recess in said neck inwardly of said male conical taper surface.

16. The set of modular components of claim 15, in which said pins of at least two of said modular head prostheses are differently sized.

17. The set of modular components of claim 16, in which the recess of at least one of said modular stem prostheses is sized to receive the pin of at least one but not all of the said modular head prostheses.

18. The set of modular components of claim 11, in which said keyed stem and head prostheses include a pin extending from at least one said stem inwardly of said male conical taper surface.

19. The set of modular components of claim 18, in which said keyed stem and head prostheses include a recess in at least one of said modular heads inwardly of said female conical taper surface.

20. The set of modular components of claim 19, in which said pin and said recess are non-round in cross-section.

21. The set of modular components of claim 19, in which said pin and said recess are located eccentrically relative to said respective stem and modular head.

* * * * *